United States Patent
Legrand et al.

(10) Patent No.: US 8,343,237 B2
(45) Date of Patent: Jan. 1, 2013

(54) COMPOSITION COMPRISING AN ALKANOLAMINE, AN AMINO ACID AND AN ASSOCIATIVE POLYMER

(75) Inventors: Frédéric Legrand, Westfield, NJ (US); Jean-Marc Ascione, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 12/809,544

(22) PCT Filed: Dec. 17, 2008

(86) PCT No.: PCT/EP2008/067787
§ 371 (c)(1),
(2), (4) Date: Feb. 4, 2011

(87) PCT Pub. No.: WO2009/080669
PCT Pub. Date: Jul. 2, 2009

(65) Prior Publication Data
US 2011/0117037 A1    May 19, 2011
US 2012/0039829 A9    Feb. 16, 2012

Related U.S. Application Data

(60) Provisional application No. 61/006,536, filed on Jan. 18, 2008.

(30) Foreign Application Priority Data

Dec. 20, 2007   (FR) .................................. 07 60142

(51) Int. Cl.
*A61Q 5/10*    (2006.01)
(52) U.S. Cl. ............. 8/405; 8/406; 8/435; 8/552; 8/562; 8/604
(58) Field of Classification Search ............... 8/405, 406, 8/435, 552, 562, 604
See application file for complete search history.

(56) References Cited

U.S. PATENT DOCUMENTS

| | | | |
|---|---|---|---|
| 7,066,965 B2 | 6/2006 | Legrand et al. | |
| 7,101,405 B2 | 9/2006 | Cottard et al. | |
| 7,364,594 B2 | 4/2008 | Cottard et al. | |
| 7,458,993 B2 | 12/2008 | Cottard et al. | |
| 7,485,156 B2 | 2/2009 | Saunier | |
| 7,569,078 B2 | 8/2009 | Legrand | |
| 7,578,854 B2 | 8/2009 | Legrand | |
| 7,645,303 B2 | 1/2010 | Cottard et al. | |
| 2005/0188480 A1* | 9/2005 | Lim et al. ........................ | 8/405 |
| 2006/0096039 A9* | 5/2006 | Rollat-Corvol et al. ......... | 8/405 |

FOREIGN PATENT DOCUMENTS

| | | |
|---|---|---|
| DE | 10 2005 059 647 A1 | 6/2007 |
| EP | 1 374 842 A1 | 1/2004 |
| EP | 1 707 182 A1 | 10/2006 |
| EP | 1 707 190 A1 | 10/2006 |
| FR | 2 816 207 A1 | 5/2002 |
| FR | 2 816 209 A1 | 5/2002 |
| FR | 2 817 467 A1 | 6/2002 |
| FR | 2 838 337 A1 | 10/2003 |
| FR | 2 886 137 A1 | 12/2006 |
| JP | 59-106413 | 6/1984 |
| JP | 2004-262885 | 9/2004 |
| JP | 2004-262886 | 9/2004 |
| WO | WO 97/04739 | 2/1997 |

OTHER PUBLICATIONS

French Search Report for FR 0760142, dated Aug. 12, 2008.
English language abstract of DE 10 2005 059 647 A1, Jun. 14, 2007.
English language abstract of JP 59-106413, Jun. 20, 1984.
English language abstract of JP 2004-262885, Sep. 24, 2004.
English language abstract of JP 2004-262886, Sep. 24, 2004.
English language abstract of WO 97/04739, Feb. 13, 1997.

* cited by examiner

*Primary Examiner* — Eisa Elhilo
(74) *Attorney, Agent, or Firm* — O'Brien Jones, PLLC

(57) ABSTRACT

The present invention provides a composition for treating keratin fibers, and especially human keratin fibers such as the hair, which comprises, in a cosmetically acceptable medium, one or more alkanolamines, one or more amino acids and one or more associative polymers. The present invention likewise provides methods of bleaching and/or coloring keratin fibers, and also multiple-compartment devices or kits for the implementation of these methods.

15 Claims, No Drawings

COMPOSITION COMPRISING AN ALKANOLAMINE, AN AMINO ACID AND AN ASSOCIATIVE POLYMER

CROSS REFERENCE TO RELATED APPLICATIONS

This application is a national phase application based on PCT/EP2008/067787, filed Dec. 17, 2008, which claims the priority of French Patent Application No. 0760142, filed Dec. 20, 2007; and claims the benefit of U.S. Provisional Application No. 61/006,536, filed Jan. 18, 2008; the content of all of which is incorporated herein by reference.

The present invention provides a composition for treating keratin fibres, and especially human keratin fibres such as the hair, which comprises, in a cosmetically acceptable medium, one or more alkanolamines, one or more amino acids and one or more associative polymers.

It is known practice, for the treatment of hair, to use oxidizing compositions, more particularly for dyeing human keratin fibres, and especially the hair, with dyeing compositions containing oxidation dye precursors, generally referred to as oxidation bases. These oxidation bases are colourless or weakly coloured compounds which, in combination with oxidizing products, give rise, by a process of oxidative condensation, to coloured compounds.

The method of oxidation dyeing involves applying, to the keratin fibres, oxidation bases, or a mixture of oxidation bases and couplers, with an oxidizing agent, such as hydrogen peroxide, which is added at the time of use.

Generally speaking, this method is implemented at an alkaline pH, more particularly in the presence of ammonia, and produces a dyeing and, at the same time, a lightening of the fibre that is manifested in practice by the possibility of obtaining an eventual coloration which is lighter than the original colour. Moreover, the lightening of the fibre has the advantageous effect of bringing about a unified colour in the case of depigmented hair, and of emphasizing the colour—that is, making it more visible—in the case of naturally pigmented hair.

It is likewise known practice to dye human keratin fibres by what is called semi-permanent coloration or direct coloration, which employs dyes that are capable of themselves providing a more or less marked modification to the natural colouring of the hair.

These direct dyes may also be used in combination with oxidizing agents, where the desire is to obtain a coloration which is lighter than the original colour of the fibres. Accordingly, these direct dyes may be used in compositions for lightening direct dyeing that are based on hydrogen peroxide and ammonia, or in compositions for oxidation dyeing in association with oxidation bases and/or couplers.

Furthermore, when a person wishes to bleach their hair, it is also known practice to carry out bleaching using lightening products based on ammonia and hydrogen peroxide.

Accordingly, it is usual to employ alkaline oxidizing compositions that are based on hydrogen peroxide and ammonia for the purpose of colouring and/or bleaching human keratin fibres, and especially the hair.

However, although these conditions of use do prove to be effective, they may give rise to a certain number of annoyances at the time of their use.

In particular, when these compositions are applied to the hair, there is generally a release of ammonia, which can lead to a suffocating odour which is irritating to the eyes, airways and mucous membranes.

Moreover, particularly in persons with a sensitive scalp, the ammonia may give rise to reactions of discomfort, such as redness, itching or pricking.

Finally, ammonia, in combination with the oxidizing agent, may also contribute to damaging the keratin fibres. Indeed, over the long term, the fibres are observed to be or more less degraded and to have a tendency to become lank, dull, fragile and difficult to style.

Accordingly, in order to remedy all of the drawbacks described above, numerous alternatives have already been proposed for the purpose of significantly reducing the levels of ammonia in compositions that are intended for the colouring and/or bleaching of fibres.

To this end, proposals have been made to apply, to the hair, colouring and/or bleaching compositions that comprise a non-volatile organic amine, such as monoethanolamine. Although such compositions do have the advantage of not releasing ammonia while they are being used, they usually give rise to reactions of discomfort, and especially to irritation in people with a sensitive scalp. Furthermore, for equivalent lightening performance, monoethanolamine damages the hair in a way which is greater than that of ammonia.

Other compositions combining ammonia with a water-soluble ammonium salt have also been envisaged. Compositions of this kind are described more particularly in patent application EP 0 148 466.

However, these compositions do not allow a satisfactory reduction in the unpleasant odours caused by the release of ammonia, and the lightening performance of this type of composition remains limited relative to that of ammonia-based compositions.

In the same way, compositions containing compounds such as ammonium, alkali metal or alkaline earth metal carbonates and hydrogen carbonates have been proposed.

Although these compositions do allow a significant reduction in the levels of ammonia, their lightening performance still remains below that of ammonia-based compositions. Moreover, these compositions continue to cause great damage to the keratin fibres.

Alternatively, compositions based on neutral or basic amino acids have been envisaged for the purpose of providing a total or partial replacement for the ammonia content.

Accordingly, patent EP 0 840 593 describes ammonia-free compositions comprising in particular, as an alkaline agent, a mixture based on a compound selected from amino acids and oligopeptides which have an amino group and a —COOH or —SO$_3$H group, and a compound selected from the group consisting of monoethanolamine, monoisopropanolamine, 2-amino-2-methylpropanol, 2-amino-2-methyl-1,3-propanediol, 2-amino-2-ethyl-1,3-propanediol and 2-amino-2-methylbutanol.

Patent applications JP 2004 262885 and JP 2004 262886 likewise describe ammonia-free compositions based on neutral or basic amino acids, non-volatile amine, and an acidic organic ammonium ion.

Finally, U.S. Pat. No. 5,131,912 describes compositions based on neutral or basic amino acids and on alkaline agents such as ammonium, alkali metal or alkaline earth metal carbonates or hydrogen carbonates. The mixture before use of these alkaline compositions with an oxidizing hydrogen peroxide composition presents a pH of between 6.5 and 7.9.

Although such compositions do have the advantage of not releasing ammonia while being used, they still do not make it possible to match the lightening performance level of the ammonia-based compositions. Furthermore, these compositions can give rise to irritation to the scalp.

Furthermore, it is customary to employ polymers for the purpose of thickening the colouring and/or bleaching compositions. Use may be made in particular of amphiphilic polymers containing at least one fatty chain, and, more preferably, of cationic or non-ionic amphiphilic polymers containing at least one fatty chain.

It is, however, often difficult to obtain textures which go on quickly and comfortably, without running, and also strong, colourful and homogeneous colorations, with the conditions of use described above, in spite of the presence of amphiphilic polymers containing at least one fatty chain.

The objective of the present invention is to reduce the levels of ammonia in the compositions intended, in particular, for colouring and/or for bleaching, so as to reduce the unpleasant odours accompanying the process, the irritations to the scalp and the damage to the keratin fibres, while retaining good colouring and/or bleaching properties and good textures in the compositions.

This objective is achieved with the present invention, which provides a composition for treating keratin fibres, comprising, in a cosmetically acceptable medium:
one or more alkanolamines;
one or more amino acids; and
one or more associative polymers.

The composition according to the invention, when mixed with a composition comprising an oxidizing agent, allows a composition to be obtained which is intended for application to keratin fibres and whose texture is ideal for quick and comfortable application, without the product running.

The composition according to the invention exhibits the advantage of minimizing, or even suppressing, the drawbacks that are caused by release of ammonia.

The composition according to the invention also allows a reduction to be achieved in the discomfort likely to be sensed at the time of application of said composition to the keratin fibres, at the scalp.

Moreover, the composition allows the damage to the fibre to be reduced, relative to conventional colouring and/or bleaching compositions containing ammonia as their primary alkaline agent.

When employed with oxidation bases and/or couplers and/or direct dyes, a colouring composition is obtained which has the further advantage of possessing good dyeing properties, and, more particularly, strong, colourful colorations which are relatively non-selective and which are highly resistant to the various forms of attack that the hair may undergo.

When the composition according to the invention is employed with an oxidizing agent, such as hydrogen peroxide, a bleaching or lightening composition is obtained which has the further advantage of leading to satisfactory lightening of the keratin fibres.

The present invention likewise provides methods of bleaching and/or colouring keratin fibres, and also provides multiple-compartment devices or kits for the implementation of these methods.

Other subjects, features, aspects and advantages of the invention will emerge more clearly from the reading of the description and the examples which follow.

In the text below, unless otherwise indicated, the end points of the ranges indicated are included in the invention.

In one particular embodiment of the invention, the alkanolamine or alkanolamines are selected from monoethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and trishydroxymethylaminomethane.

Preference is given to using monoethanolamine.

The alkanolamine or alkanolamines are generally present in the composition in accordance with the invention in an amount of between 0.1% and 15% by weight, preferably between 0.5% and 10% by weight, and more preferably between 1% and 7% by weight of the total weight of the composition.

In one particular embodiment of the invention, the amino acid or acids contain one or more amine functions and one or more acid functions. The acid function or functions may be carboxylic, sulphonic, phosphonic or phosphoric, and preferably carboxylic.

The amino acids present in the composition in accordance with the invention preferably have a molecular weight of less than 500.

In one particular embodiment of the invention, the amino acid or acids present in the composition in accordance with the present invention are α-amino acids, which is to say that they contain an amine function and a group R which are situated in the alpha position in relation to the acid function. They may, for example, be represented by the formula:

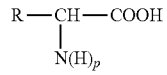

in which:
p is 1 or 2;
R represents a hydrogen atom, an aliphatic group containing or not containing a heterocyclic moiety, or an aromatic group; where p=1, R may also form, with the nitrogen atom of —N(H)$_p$, a heterocycle. This heterocycle is preferably a saturated, 5-membered ring which is optionally substituted by one or more C$_{1-4}$ alkyl groups, or hydroxyl.

The aliphatic group is preferably a linear or branched C$_1$-C$_4$ alkyl group; a linear or branched C$_1$-C$_4$ hydroxyalkyl group; a linear or branched C$_1$-C$_{44}$ aminoalkyl group; a linear or branched C$_1$-C$_4$ (C$_1$-C$_4$ alkyl)thioalkyl group; a linear or branched C$_2$-C$_4$ carboxyalkyl group; a linear or branched ureidoalkyl group, a linear or branched guanidinoalkyl group, a linear or branched imidazoloalkyl group, or a linear or branched indoylalkyl group, the alkyl moieties of these last four groups containing one to four carbon atoms.

The aromatic group is preferably a C$_6$ aryl or C$_7$-C$_{10}$ aralkyl group, the aromatic nucleus being optionally substituted by one or more C$_1$-C$_4$ alkyl groups, or hydroxyl.

Amino acids which can be used in the present invention include, more particularly, aspartic acid, glutamic acid, alanine, arginine, aspartic acid, glutamine, glycine, histidine, isoleucine, leucine, lysine, methionine, N-phenylalanine, proline, serine, threonine, tryptophan, tyrosine, valine and hydroxyproline.

The amino acids that are particularly preferred in the present invention are arginine, glycine, histidine, and lysine.

The compositions employed in accordance with the invention generally have a concentration of amino acid(s) of between 0.1% and 15% by weight, preferably between 0.5% and 10% by weight, and more preferably between 1% and 10% by weight, relative to the total weight of the composition.

In one particular embodiment of the invention the alkanolamines/amino acids molar ratio is greater than or equal to 0.1, preferably greater than or equal to 1. More preferably still this ratio is greater than or equal to 1.5.

In another particular embodiment of the invention the alkanolamines/amino acids molar ratio is less than or equal to 50, preferably less than or equal to 10.

The associative polymers are water-soluble polymers which in an aqueous medium are capable of undergoing reversible association with one another or with other molecules. Their chemical structure includes hydrophilic zones and hydrophobic zones which are characterized by at least one fatty chain.

The associative polymers according to the invention may be anionic, cationic, amphoteric or non-ionic. The associative polymers are preferably cationic or non-ionic.

Anionic associative polymers include:

(I) those containing at least one hydrophilic unit and at least one fatty-chain allyl ether unit, more particularly those whose hydrophilic unit is composed of an ethylenically unsaturated anionic monomer, more particularly still of a vinyl carboxylic acid, and very particularly of an acrylic acid or a methacrylic acid or mixtures thereof, and whose fatty-chain allyl ether unit corresponds to the monomer of formula (I) below:

$$CH_2=CR'CH_2OB_nR \quad (I)$$

in which R' is H or $CH_3$, B is the ethyleneoxy radical,
n is zero or is an integer ranging from 1 to 100, R is a hydrocarbon radical selected from alkyl, arylalkyl, aryl, alkylaryl and cycloalkyl radicals containing 8 to carbon atoms, preferably 10 to 24, and more particularly 12 to 18 carbon atoms. A more particularly preferred unit of formula (I) is a unit in which R' is H, n is 10 and R is a stearyl ($C_{18}$) radical.

Anionic associative polymers of this type are described and prepared, by an emulsion polymerization process, in patent EP-0 216 479.

Among these anionic associative polymers, particular preference is given in accordance with the invention to the polymers formed from 20% to 60% by weight of acrylic acid and/or methacrylic acid, from 5% to 60% by weight of lower alkyl(meth)acrylates, from 2% to 50% by weight of fatty-chain allyl ether of formula (I), and from 0% to 1% by weight of a crosslinking agent which is a well-known copolymerizable polyethylenic unsaturated monomer, such as diallyl phthalate, allyl (meth)acrylate, divinylbenzene, (poly)ethylene glycol dimethacrylate and methylenebisacrylamide.

Among the latter, very particular preference is given to the crosslinked terpolymers of methacrylic acid, ethyl acrylate and polyethylene glycol (10 EO) ether of stearyl alcohol (Steareth 10), especially those sold by Allied Colloids under the names Salcare SC 80® and Salcare SC90®, which are aqueous emulsions containing 30% of a crosslinked terpolymer of methacrylic acid, ethyl acrylate and steareth-10-allyl ether (40/50/10).

(II) those containing at least one hydrophilic unit of olefinic unsaturated carboxylic acid type, and at least one hydrophobic unit of unsaturated carboxylic acid alkyl ($C_{10}$-$C_{30}$) ester type.

Preferably these polymers are selected from those whose hydrophilic unit of olefinic unsaturated carboxylic acid type corresponds to the monomer of formula (II) below:

(II)

in which $R_1$ is H or $CH_3$ or $C_2H_5$, in other words acrylic acid, methacrylic acid or ethacrylic acid units, and whose hydrophobic unit of unsaturated carboxylic acid alkyl ($C_{10}$-$C_{30}$ ester type corresponds to the monomer of formula (III) below:

(III)

in which $R_2$ is H or $CH_3$ or $C_2H_5$ (in other words, acrylate, methacrylate or ethacrylate units) and preferably H (acrylate units) or $CH_3$ (methacrylate units), $R_3$ being a $C_{10}$-$C_{30}$, and preferably $C_{12}$-$C_{22}$, alkyl radical.

Unsaturated carboxylic acid alkyl ($C_{10}$-$C_{30}$) esters in accordance with the invention comprise, for example, lauryl acrylate, stearyl acrylate, decyl acrylate, isodecyl acrylate, dodecyl acrylate, and the corresponding methacrylates, lauryl methacrylate, stearyl methacrylate, decyl methacrylate, isodecyl methacrylate and dodecyl methacrylate.

Anionic polymers of this type are, for example, described and prepared according to U.S. Pat. Nos. 3,915,921 and 4,509,949.

Among this type of anionic associative polymers, use will be made more particularly of polymers formed from a mixture of monomers comprising:
(i) essentially acrylic acid,
(ii) an ester of formula (III) described above, in which $R_2$ is H or $CH_3$, $R_3$ being an alkyl radical having 12 to 22 carbon atoms,
(iii) and a crosslinking agent, which is a well-known, copolymerizable, polyethylenic, unsaturated monomer, such as diallyl phthalate, allyl(meth)acrylate, divinylbenzene, (poly)ethylene glycol dimethacrylate and methylenebisacrylamide.

Among this type of anionic associative polymer, use will be made more particularly of those composed of 95% to 60% by weight of acrylic acid (hydrophilic unit), 4% to 40% by weight of $C_{10}$-$C_{30}$ alkyl acrylate (hydrophobic unit) and 0% to 6% by weight of crosslinking polymerizable monomer, or else of those composed of 98% to 96% by weight of acrylic acid (hydrophilic unit), 1% to 4% by weight of $C_{10}$-$C_{30}$ alkyl acrylate (hydrophobic unit), and 0.1% to 0.6% by weight of crosslinking polymerizable monomer, such as those described above.

Among said polymers above, very particular preference, in accordance with the present invention, will be given to the products sold by Goodrich under the trade names Pemulen TR1®, Pemulen TR2®, Carbopol 1382®, and more preferably to Pemulen TR10, and to the product sold by SEPPIC under the name Coatex SX®.

(III) maleic anhydride/$C_{30}$-$C_{38}$ α-olefin/alkyl maleate terpolymers such as the product (maleic anhydride/$C_{30}$-$C_{38}$ α-olefin/isopropyl maleate copolymer) sold under the name Performa V 1608® by Newphase Technologies.

(IV) acrylic terpolymers containing:
(a) approximately 20% to 70% by weight of an α,β-monoethylenically unsaturated carboxylic acid,
(b) approximately 20% to 80% by weight of a non-surfactant α,β-monoethylenically unsaturated monomer other than (a),
(c) approximately 0.5% to 60% by weight of a non-ionic monourethane which is the reaction product of a monohydric surfactant with a monoisocyanate containing monoethylenic unsaturation,
such as those described in patent application EP-A-0173109, and more particularly that described in Example 3, namely a terpolymer of methacrylic acid/methyl acrylate/dimethyl metaisopropenyl benzyl isocyanate of ethoxylated (40 EO) behenyl alcohol, in aqueous dispersion at 25%.

(V) the copolymers containing, among their monomers, an α,β-monoethylenically unsaturated carboxylic acid and an ester of an α,β-monoethylenically unsaturated carboxylic acid and an alkoxylated fatty alcohol.

These compounds preferably further comprise as monomer an ester of an α,β-monoethylenically unsaturated carboxylic acid and a $C_1$-$C_4$ alcohol.

An example of this type of compound is Aculyn 22® sold by Rohm and Haas, which is a methacrylic acid/ethyl acrylate/alkyloxylated stearyl methacrylate terpolymer.

The cationic associative polymers include:

(I) cationic associative polyurethanes of the class described by the applicant in French patent application No. 0009609; it may be represented by the general formula (IV) below:

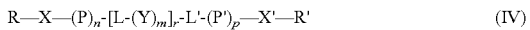

$$R—X—(P)_n\text{-}[L\text{-}(Y)_m]_r\text{-}L'\text{-}(P')_p—X'—R' \quad (IV)$$

in which:

R and R', which are identical or different, represent a hydrophobic group or a hydrogen atom;
X and X', which are identical or different, represent a group containing an amine function which does or does not carry a hydrophobic group, or else the group L";
L, L' and L", which are identical or different, represent a group derived from a diisocyanate;
P and P', which are identical or different, represent a group containing an amine function which does or does not carry a hydrophobic group;
Y represents a hydrophilic group;
r is an integer between 1 and 100, preferably between 1 and 50 and in particular between 1 and 25,
n, m, and p, each independently of the others, is between 0 and 1000;
and the molecule contains at least one protonated or quaternized amine function and at least one hydrophobic group.

In one preferred embodiment of these polyurethanes, the only hydrophobic groups are the groups R and R' at the chain ends.

A preferred class of cationic associative polyurethanes is that corresponding to the formula (IV) described above in which:
R and R' both, independently, represent a hydrophobic group,
X and X' each represent a group L",
n and p are between 1 and 1000, and
L, L', L", P, P', Y and m have the meaning indicated above.

Another preferred class of cationic associative polyurethanes is that corresponding to the formula (IV) above, in which:
R and R' both represent, independently, a hydrophobic group,
X and X' each represent a group L", n and p are 0, and L, L', L", Y and m are as defined above.

The fact that n and p are 0 means that these polymers contain no units derived from an amine-functional monomer incorporated into the polymer in the course of the polycondensation. The protonated amine functions of these polyurethanes result from the hydrolysis of isocyanate functions, in excess, at the chain end, followed by the alkylation of the primary amine functions formed by alkylating agents containing a hydrophobic group, in other words compounds of type RQ or R'Q, in which R and R' are as defined above and Q denotes a leaving group such as a halide, a sulphate, etc.

Yet another preferred class of cationic associative polyurethanes is that corresponding to the formula (IV) above in which:

R and R' both represent, independently, a hydrophobic group,
X and X' both represent, independently, a group containing a quaternary amine,
n and p are zero, and
L, L', Y and m are as defined above.

The number-average molecular mass of the cationic associative polyurethanes is preferably between 400 and 500 000, in particular between 1000 and 400 000 and ideally between 1000 and 300 000.

By a hydrophobic group is meant a radical or polymer containing a linear or branched, saturated or unsaturated hydrocarbon chain which may contain one or more heteroatoms such as P, O, N, S, or a radical having a perfluorinated or silicone chain. When it denotes a hydrocarbon radical, the hydrophobic group contains at least 10 carbon atoms, preferably 10 to 30 carbon atoms, in particular 12 to 30 carbon atoms and more preferably 18 to 30 carbon atoms.

The hydrocarbon group preferably originates from a monofunctional compound.

By way of example, the hydrophobic group may be obtained from a fatty alcohol such as stearyl alcohol, dodecyl alcohol or decyl alcohol. It may also denote a hydrocarbon polymer such as, for example, polybutadiene.

When X and/or X' denote a group containing a tertiary or quaternary amine, X and/or X' may represent one of the following formulae:

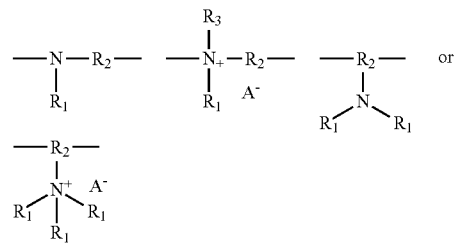

for X

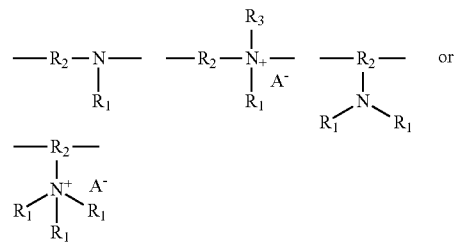

for X' in which:

$R_2$ represents an alkylene radical having 1 to 20 carbon atoms which is linear or branched and contains or does not contain a saturated or unsaturated ring, or an arylene radical, it being possible for one or more of the carbon atoms to be replaced by a heteroatom selected from N, S, O and P;

$R_1$ and $R_3$, which are identical or different, denote a linear or branched $C_1$-$C_{30}$ alkyl or alkenyl radical, or an aryl radical, it being possible for at least one of the carbon atoms to be replaced by a heteroatom selected from N, S, O and P;

$A^-$ is a physiologically acceptable counter-ion.

The groups L, L' and L" represent a group of formula:

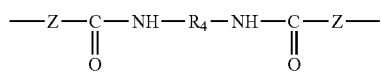

in which:
Z represents —O—, —S— or —NH—; and
$R_4$ represents a linear or branched alkylene radical which has 1 to 20 carbon atoms, and contains or does not contain a saturated or unsaturated ring, or an arylene radical, it being possible for one or more of the carbon atoms to be replaced by a heteroatom selected from N, S, O and P.

The groups P and P', containing an amine function, may represent at least one of the following formulae:

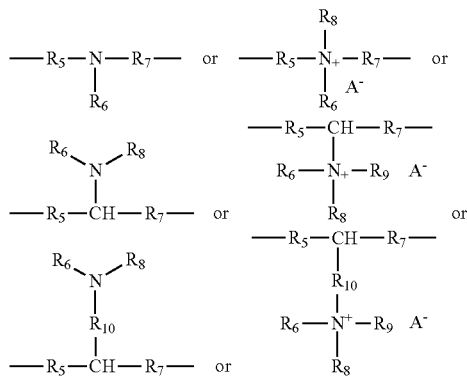

in which:
$R_5$ and $R_7$ have the same meanings as $R_2$ defined above;
$R_6$, $R_8$ and $R_9$ have the same meanings as $R_1$ and $R_3$ defined above;
$R_{10}$ represents a linear or branched alkylene group which is optionally unsaturated and may contain one or more heteroatoms selected from N, O, S and P,
and $A^-$ is a physiologically acceptable counter-ion.

With regard to the meaning of Y, a hydrophilic group is a polymeric or non-polymeric, water-soluble group.

As an example, mention may be made, in the case where the polymers are not involved, of ethylene glycol, diethylene glycol and propylene glycol.

When, in accordance with one preferred embodiment, a hydrophilic polymer is involved, mention may be made, by way of example, of polyethers, sulphonated polyesters, sulphonated polyamides, or a mixture of these polymers. Preferentially the hydrophilic compound is a polyether, and more particularly a poly(ethylene oxide) or poly(propylene oxide).

The cationic associative polyurethanes of formula (IV) according to the invention are formed from diisocyanates and from various compounds possessing functions containing labile hydrogen. The functions containing labile hydrogen may be alcohol, primary or secondary amine or thiol functions which give rise, after reaction with the diisocyanate functions, respectively to polyurethanes, to polyureas and to polythioureas. The term "polyurethanes" of the present invention encompasses these three types of polymers—that is, the polyurethanes proper, the polyureas and the polythioureas, and also copolymers of these.

A first type of compound entering into the preparation of the polyurethane of formula (IV) is a compound containing at least one amine-functional unit. This compound may be polyfunctional, but preferably the compound is difunctional, which is to say that, in one preferred embodiment, this compound contains two atoms of labile hydrogen which are carried, for example, by a hydroxyl, primary amine, secondary amine or thiol function. It is also possible to use a mixture of polyfunctional and difunctional compounds in which the percentage of polyfunctional compounds is low.

As indicated above, this compound may contain more than one amine-functional unit. In that case it is a polymer carrying a repetition of the amine-functional unit.

This type of compounds may be represented by one of the following formulae:

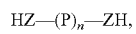

or

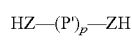

in which Z, P, P', n and p are as defined above.
Examples of amine-functional compounds include N-methyldiethanolamine, N-tert-butyldiethanolamine and N-sulphoethyldiethanolamine.

The second compound involved in the preparation of the polyurethane of formula (IV) is a diisocyanate corresponding to the formula:

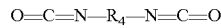

in which $R_4$ is defined earlier on above.
Examples include methylenediphenyl diisocyanate, methylenecyclohexane diisocyanate, isophorone diisocyanate, toluene diisocyanate, naphthalene diisocyanate, butane diisocyanate and hexane diisocyanate.

A third compound involved in the preparation of the polyurethane of formula (IV) is a hydrophobic compound intended for forming the terminal hydrophobic groups of the polymer of formula (IV).

This compound is composed of a hydrophobic group and a function containing labile hydrogen, a hydroxyl, primary or secondary amine or thiol function, for example.

By way of example, this compound may be a fatty alcohol, such as, more particularly, stearyl alcohol, dodecyl alcohol or decyl alcohol. When this compound contains a polymeric chain it may be, for example, α-hydroxy hydrogenated polybutadiene.

The hydrophobic group of the polyurethane of formula (IV) may also result from the quaternization reaction of the tertiary amine of the compound containing at least one tertiary amine unit. Accordingly, the hydrophobic group is introduced by the quaternizing agent. This quaternizing agent is a compound RQ or R'Q in which R and R' are as defined above and Q denotes a leaving group such as a halide, a sulphate, etc.

The cationic associative polyurethane may further comprise a hydrophilic sequence. This sequence is provided by a fourth type of compound involved in the preparation of the polymer. This compound may be polyfunctional. It is preferably difunctional. It is also possible to have a mixture in which the percentage of polyfunctional compound is low.

The functions containing labile hydrogen are alcohol, primary or secondary amine or thiol functions. This compound may be a polymer terminated at the chain ends with one of these functions containing labile hydrogen.

By way of example, when the compound involved is not a polymer, mention may be made of ethylene glycol, diethylene glycol and propylene glycol.

When the compound involved is a hydrophilic polymer, mention may be made, by way of example, of polyethers, sulphonated polyesters, sulphonated polyamides or a mixture of these polymers. Preferably the hydrophilic compound is a polyether, and more particularly a poly(ethylene oxide) or poly(propylene oxide).

The hydrophilic group labelled Y in the formula (IV) is optional. Indeed, the units containing a protonated or quaternary amine function may be enough to provide the solubility or water-dispersibility required for this type of polymer in an aqueous solution.

Although the presence of a hydrophilic group Y is optional, preference is nevertheless given to cationic associative polyurethanes which contain such a group.

(II) quaternized cellulose derivatives and polyacrylates containing non-cyclic amine side groups.

Quaternized cellulose derivatives are in particular:
quaternized celluloses modified with groups containing at least one fatty chain, such as alkyl, arylalkyl and alkylaryl groups containing at least 8 carbon atoms, or mixtures thereof;
quaternized hydroxyethylcelluloses modified with groups containing at least one fatty chain, such as alkyl, arylalkyl and alkylaryl groups containing at least 8 carbon atoms, or mixtures thereof.

The alkyl radicals carried by the quaternized celluloses or hydroxyethylcelluloses above preferably contain 8 to 30 carbon atoms. The aryl radicals are preferably phenyl, benzyl, naphthyl or anthryl groups.

Examples that may be indicated of quaternized alkylhydroxyethylcelluloses containing $C_8$-$C_{30}$ fatty chains are the products Quatrisoft LM 200®, Quatrisoft LM-X 529-18-A®, Quatrisoft LM-X 529-18B® ($C_{1-2}$ alkyl) and Quatrisoft LM-X 529-8® ($C_{18}$ alkyl), which are sold by Amerchol, and the products Crodacel QM®, Crodacel QL® ($C_{1-2}$ alkyl) and Crodacel QS® ($C_{1-8}$ alkyl), which are sold by Croda.

(III) The cationic polyvinyllactams whose family was described by the Applicant in French patent application No. 0101106.

Said polymers comprise:
a) at least one vinyllactam or alkylvinyllactam monomer,
b) at least one monomer of structure (V) or (VI) below:

$R_8$ denotes a hydrogen atom or a linear or branched $C_1$-$C_{30}$ alkyl radical,
p, q and r denote, independently of one another, either the value zero or the value 1,
m and n denote, independently of one another, an integer ranging from 0 to 100,
x denotes an integer ranging from 1 to 100,
Z denotes an organic or inorganic acid anion,
with the provisos that:
one at least of the substituents $R_3$, $R_4$, $R_5$ or $R_8$ denotes a linear or branched $C_9$-$C_{30}$ alkyl radical,
if m or n is other than zero, q is 1,
if m or n is equal to zero, p or q is 0.

The cationic poly(vinyllactam) polymers according to the invention may be crosslinked or non-crosslinked and may also be block polymers.

The counter-ion Z– of the monomers of formula (V) is preferably selected from halide ions, phosphate ions, methosulphate ion and tosylate ion.

$R_3$, $R_4$ and $R_5$ preferably denote, independently of one another, a hydrogen atom or a linear or branched $C_1$-$C_{30}$ alkyl radical.

More preferably the monomer (b) is a monomer of formula (v) for which, more preferably still, m and n are equal to zero.

The vinyllactam or alkylvinyllactam monomer is preferably a compound of structure (VIII):

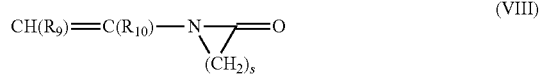

in which:
s denotes an integer ranging from 3 to 6,
$R_9$ denotes a hydrogen atom or a $C_1$-$C_5$ alkyl radical,
$R_{10}$ denotes a hydrogen atom or a $C_1$-$C_5$ alkyl radical,
with the proviso that at least one of the radicals $R_9$ and $R_{10}$ denotes a hydrogen atom.

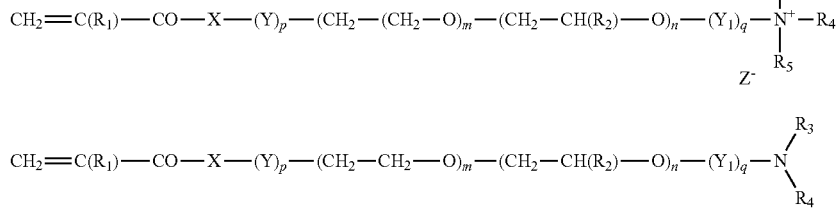

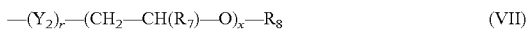

in which:
X denotes an oxygen atom or a radical $NR_6$,
$R_1$ and $R_6$ denote, independently of one another, a hydrogen atom or a linear or branched $C_1$-$C_5$ alkyl radical,
$R_2$ denotes a linear or branched $C_1$-$C_4$ alkyl radical,
$R_3$, $R_4$ and $R_5$ denote, independently of one another, a hydrogen atom, a linear or branched $C_1$-$C_{30}$ alkyl radical or a radical of formula (VII):

—$(Y_2)_r$—$(CH_2$—$CH(R_7)$—$O)_x$—$R_8$      (VII)

Y, $Y_1$ and $Y_2$ denote, independently of one another, a linear or branched $C_2$-$C_{16}$ alkylene radical,
$R_7$ denotes a hydrogen atom, a linear or branched $C_1$-$C_4$ alkyl radical or a linear or branched $C_1$-$C_4$ hydroxyalkyl radical, More preferably still, the monomer (VIII) is vinylpyrrolidone.

The cationic poly(vinyllactam) polymers according to the invention may also contain one or more further monomers, preferably cationic or non-ionic monomers.

Compounds more particularly preferred according to the invention include the following terpolymers comprising at least:

a)—a monomer of formula (VIII),
b)—a monomer of formula (V) in which p=1, q=0, $R_3$ and $R_4$ denote, independently of one another, a hydrogen atom or a $C_1$-$C_5$ alkyl radical and $R_5$ denotes a $C_9$-$C_{24}$ alkyl radical, and c)—a monomer of formula (VI) in which $R_3$ and $R_4$ denote, independently of one another, a hydrogen atom or a $C_1$-$C_5$ alkyl radical.

Still more preference is given to using the terpolymers comprising, by weight, 40% to 95% of monomer (a), 0.1% to 55% of monomer (c) and 0.25% to 50% of monomer (b).

Polymers of this kind are described in patent application WO-00/68282, whose content forms an integral part of the invention.

Cationic poly(vinyllactam) polymers according to the invention that are used are, in particular, vinylpyrrolidone/dimethylaminopropylmethacrylamide/dodecyldimethylmethacrylamidopropylammonium tosylate terpolymers, vinylpyrrolidone/dimethylaminopropylmethacrylamide/cocoyldimethylmethacrylamidopropylammonium tosylate terpolymers, and vinylpyrrolidone/dimethylaminopropylmethacrylamide/lauryldimethylmethacrylamidopropylammonium chloride or tosylate terpolymers.

The weight-average molecular mass of the cationic poly(vinyllactam) polymers according to the present invention is preferably between 500 and 20 000 000. More particularly it is between 200 000 and 2 000 000, and more preferably still between 400 000 and 800 000.

The amphoteric associative polymers are selected preferably from those including at least one non-cyclic cationic unit. More particularly, preference is given to those prepared from or containing 1 to 20 mol % of monomer containing a fatty chain, and preferably 1.5 to 15 mol % and more particularly 1.5 to 6 mol %, relative to the total number of moles of monomers.

The preferred amphoteric associative polymers according to the invention comprise or are prepared by copolymerizing:
1) at least one monomer of formula (IXa) or (IXb):

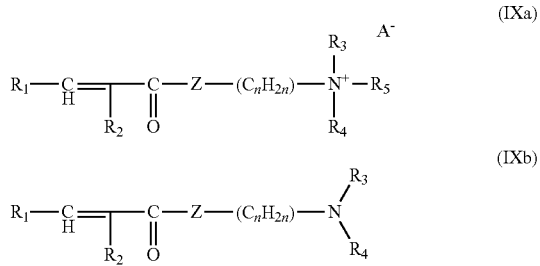

in which $R_1$ and $R_2$, which are identical or different, represent a hydrogen atom or a methyl radical, $R_3$, $R_4$ and $R_5$, which are identical or different, represent a linear or branched alkyl radical having 1 to 30 carbon atoms,
Z represents an NH group or an oxygen atom,
n is an integer from 2 to 5,
A– is an anion obtained from an organic or inorganic acid, such as a methosulphate anion or a halide such as chloride or bromide;
2) at least one monomer of formula (X):

in which $R_6$ and $R_7$, which are identical or different, represent a hydrogen atom or a methyl radical; and
3) at least one monomer of formula (XI):

in which $R_6$ and $R_7$, which are identical or different, represent a hydrogen atom or a methyl radical, X denotes an oxygen or nitrogen atom and $R_8$ denotes a linear or branched alkyl radical having 1 to 30 carbon atoms;
where at least one of the monomers of formula (IXa), (IXb) or (XI) contains at least one fatty chain.

The monomers of formula (IXa) and (IXb) of the present invention are selected, preferably, from the group consisting of:
dimethylaminoethyl methacrylate, dimethylaminoethyl acrylate,
diethylaminoethyl methacrylate, diethylaminoethyl acrylate,
dimethylaminopropyl methacrylate, dimethylaminopropyl acrylate,
dimethylaminopropylmethacrylamide, dimethylaminopropylacrylamide,
these monomers being optionally quaternized, for example by a $C_1$-$C_4$ alkyl halide or a di-$C_1$-$C_4$ alkyl sulphate.

More particularly the monomer of formula (IXa) is selected from acrylamidopropyltrimethylammonium chloride and methacrylamidopropyltrimethylammonium chloride.

The monomers of formula (X) of the present invention are selected, preferably, from the group consisting of acrylic acid, methacrylic acid, crotonic acid and 2-methyl crotonic acid. More particularly the monomer of formula (X) is acrylic acid.

The monomers of formula (XI) of the present invention are selected, preferably, from the group consisting of $C_{12}$-$C_{22}$, and more particularly $C_{16}$-$C_{18}$, alkyl acrylates or methacrylates.

The monomers forming the fatty-chain amphoteric polymers of the invention are preferably already neutralized and/or quaternized.

The ratio of the number of cationic charges/anionic charges is preferably approximately 1.

The amphoteric associative polymers according to the invention preferably contain from 1 to 10 mol % of the monomer containing a fatty chain (monomer of formula (IXa), (IXb) or (XI)), and preferably from 1.5 to 6 mol %.

The weight-average molecular weights of the amphoteric associative polymers according to the invention may range from 500 to 50 000 000 and are preferably between 10 000 and 5 000 000.

The amphoteric associative polymers according to the invention may also contain other monomers, such as non-ionic monomers, and, in particular, such as $C_1$-$C_4$ alkyl acrylates or methacrylates.

Amphoteric associative polymers according to the invention are, for example, described and prepared in patent application WO 9844012.

Preferred among the amphoteric associative polymers according to the invention are acrylic acid/(meth)acrylamidopropyltrimethylammonium chloride/stearyl methacrylate terpolymers.

According to the invention, the non-ionic associative polymers are selected preferably from:
(1) celluloses modified with groups containing at least one fatty chain.
Examples include:
hydroxyethylcelluloses modified with groups containing at least one fatty chain, such as alkyl, arylalkyl and alkylaryl groups or mixtures thereof, and in which the alkyl groups are preferably $C_8$-$C_{22}$, such as the product Natrosol Plus Grade 330 CS® ($C_{16}$ alkyls), sold by Aqualon, or the product Bermocoll EHM 100® sold by Berol Nobel, those modified with alkylphenol polyalkylene glycol ether groups, such as the product Amercell Polymer HM-1500® (nonylphenol polyethylene glycol (15) ether), sold by Amerchol.

(2) hydroxypropylguars modified with groups containing at least one fatty chain, such as the product Esaflor HM 22® ($C_{2-2}$ alkyl chain), sold by Lamberti, and the products RE210-18® ($C_{1-4}$ alkyl chain) and RE205-1® ($C_{20}$ alkyl chain), sold by Rhone Poulenc.

(3) copolymers of vinylpyrrolidone and fatty-chain hydrophobic monomers, including, for example:
the products Antaron V216® or Ganex V216® (vinylpyrrolidone/hexadecene copolymer), sold by ISP
the products Antaron V220® or Ganex V220® (vinylpyrrolidone/eicosene copolymer), sold by ISP.

(4) Copolymers of $C_1$-$C_6$ alkyl acrylates or methacrylates and amphiphilic monomers containing at least one fatty chain, such as, for example, the ethoxylated stearyl acrylate/methyl acrylate copolymer sold by Goldschmidt under the name Antil 208®.

(5) Copolymers of hydrophilic acrylates or methacrylates and hydrophobic monomers containing at least one fatty chain, such as, for example, polyethylene glycol methacrylate/lauryl methacrylate copolymer.

(6) Polyether polyurethanes containing in their chain not only hydrophilic sequences, usually of polyethoxylated type, but also hydrophobic sequences, which may be solely aliphatic chain sequences and/or cycloaliphatic and/or aromatic chain sequences.

(7) Polymers having an aminoplast ether backbone, possessing at least one fatty chain, such as the Pure Thix® compounds available from Sud-Chemie.

The polyurethane polyethers preferably contain at least two lipophilic hydrocarbon chains, having 6 to 30 carbon atoms, separated by a hydrophilic sequence, it being possible for the hydrocarbon chains to be pendant chains or chains at the end of a hydrophilic sequence. In particular it is possible for there to be one or more pendant chains. Moreover, the polymer may contain a hydrocarbon chain at one end or at the two ends of a hydrophilic sequence.

The polyurethane polyethers may be multiple-sequence polymers, particularly in triblock form. The hydrophobic sequences may be at each end of the chain (for example: triblock copolymer with central hydrophilic sequence) or may be distributed both at the ends and within the chain (multiple-sequence copolymer, for example). These same polymers may also be graft or star polymers.

The non-ionic, fatty-chain polyurethane polyethers may be triblock copolymers whose hydrophilic sequence is a polyethoxylated chain containing from 50 to 1000 ethoxy groups. The non-ionic polyurethane polyethers contain a urethane bond between the hydrophilic sequences, this being the origin of the name.

By extension, the non-ionic, fatty-chain polyurethane polyethers also include those in which the hydrophilic sequences are linked to the lipophilic sequences by other chemical bonds.

Examples of non-ionic, fatty-chain polyurethane polyethers which can be used in the invention also include Rheolate 205®, containing a urea function and sold by Rheox, or else Rheolates® 208, 204 or 212, and also Acrysol RM 184®.

Mention may also be made of the product ELFACOS T210®, containing a $C_{12}$-$C_{14}$ alkyl chain, and of the product ELFACOS T212®, containing a $C_{18}$ alkyl chain, from Akzo.

The product DW 1206B® from Rohm & Haas, containing a $C_{20}$ alkyl chain and a urethane bond, available at 20% solids in water, can also be used.

It is also possible to use solutions or dispersions of these polymers, especially in water or in an aqueous-alcoholic medium. Examples of such polymers include Rheolate® 255, Rheolate® 278 and Rheolate® 244, which are sold by Rheox. Use may also be made of the product DW 1206F and DW 1206J, which are available from Rohm & Haas.

The polyurethane polyethers which can be used according to the invention are in particular those described in the article by G. Fonnum, J. Bakke and Fk. Hansen—Colloid Polym. Sci 271, 380-389 (1993).

More particularly still, according to the invention, it is preferred to use a polyurethane polyether obtainable by polycondensation of at least three compounds including (i) at least one polyethylene glycol containing from 150 to 180 moles of ethylene oxide, (ii) stearyl alcohol or decyl alcohol, and (iii) at least one diisocyanate.

Polyurethane polyethers of this kind are sold in particular by Rohm & Haas under the names Aculyn 46® and Aculyn 44® [Aculyn 46® is a polyethylene glycol polycondensate with 150 or 180 moles of ethylene oxide, stearyl alcohol and methylenebis(4-cyclohexyl isocyanate) (SMDI), and 15% by weight in a matrix of maltodextrin (4%) and water (81%); Aculyn 44® is a polyethylene glycol polycondensate with 150 or 180 moles of ethylene oxide, decyl alcohol and methylenebis(4-cyclohexyl isocyanate) (SMDI), at 35% by weight in a mixture of propylene glycol (39%) and water (26%)].

In one preferred composition according to the present invention, the associative polymers are selected from those of non-ionic or cationic type, more particularly from polyether polyurethanes having hydrophilic and hydrophobic sequences, polymers with an aminoplast ether backbone that contain at least one fatty chain, cationic associative polyurethanes, quaternized cellulose derivatives containing at least one fatty chain, and cationic polyvinyllactams.

In one particular embodiment the associative polymer is selected from quaternized alkyl($C_8$-$C_{30}$)hydroxyethyl-celluloses, and especially quaternized laurylhydroxy-ethylcellulose.

In one preferred embodiment of the invention the associative polymer or polymers are selected from polyurethanes and cellulose derivatives.

The concentration of associative polymers in the composition in accordance with the invention is generally between 0.01% to 10% by weight, preferably between 0.1% and 5% by weight of the total weight of the composition.

In one particular embodiment the composition in accordance with the present invention comprises monoethanolamine, arginine and polyquaternium-24.

In another particular embodiment the composition in accordance with the present invention comprises monoethanolamine, 2-amino 2-methylpropan-1-ol, lysine and cetylhydroxyethylcellulose.

In another particular embodiment the composition in accordance with the present invention comprises monoethanolamine, hystidine and cetylhydroxyethylcellulose.

The composition in accordance with the invention may comprise at least one additional alkaline agent.

In one particular embodiment of the invention, the additional alkaline agent or agents are selected from alkali metal or alkaline earth metal silicates.

The alkali metals or alkaline earth metals may be selected from lithium, sodium, potassium, magnesium, calcium and barium.

The additional alkaline agent is preferably sodium metasilicate.

The composition in accordance with the invention preferably does not contain ammonia.

When present, the additional alkaline agent or agents represent preferably from 0.1% to 5% by weight, approximately, of the total weight of the colouring composition, and more preferably from 0.1% to 3% by weight, approximately.

In one particular embodiment of the invention the composition comprises monoethanolamine, one or more amino acids, one or more associative polymers and sodium metasilicate.

The composition in accordance with the present invention preferably comprises monoethanolamine, arginine, polyquaternium-24 and sodium metasilicate.

The composition in accordance with the invention may comprise one or more oxidizing agents selected, for example, from hydrogen peroxide, urea peroxide, alkali metal bromates, persalts such as perborates and persulphates, and enzymes such as peroxidases and two electron or four electron oxidoreductases. The use of hydrogen peroxide is particularly preferred.

The oxidizing agent content of the composition may be between 0.1% and 10% by weight of the composition, preferably between 0.5% and 6% by weight of the composition.

The pH of the composition after mixing with the oxidizing agent or agents is generally between 5.5 and 10.5, preferably between 6 and 10.

The composition in accordance with the invention may also comprise various adjuvants which are commonly used in hair treatment compositions, such as anionic, cationic, nonionic, amphoteric and zwitterionic surfactants or mixtures thereof, cationic, anionic, non-ionic, amphoteric and zwitterionic polymers or mixtures thereof, organic or inorganic thickeners other than the associative polymers as described above, reducing agents or antioxidants other than the dithionites, and also penetrants, sequestrants, perfumes, buffers, dispersants, conditioning agents such as, for example, modified or unmodified, volatile or non-volatile silicones, and also film formers, ceramides, preservatives and opacifiers.

The above adjuvants are generally present in an amount in each case of between 0.01% and 20% by weight, relative to the weight of the composition.

A cosmetically acceptable medium for the purposes of the present invention is a medium which is compatible with the keratin fibres, and more particularly the hair.

The medium appropriate for the composition according to the invention is a cosmetically acceptable medium which generally comprises water or a mixture of water and one or more organic solvents. Organic solvents include, for example, the $C_1$-$C_4$ lower alkanols, such as ethanol and isopropanol; polyols and polyol ethers such as 2-butoxyethanol, propylene glycol, glycerol, propylene glycol monomethyl ether, diethylene glycol monoethyl and monomethyl ether, and also aromatic alcohols such as benzyl alcohol or phenoxyethanol, and mixtures thereof.

The solvents are preferably present in proportions of between 1% and 40% by weight, approximately, relative to the total weight of the cosmetic composition, and more preferably between 5% and 30% by weight, approximately.

The person skilled in the art will of course ensure that this or these optional complementary compounds are chosen such that the advantageous properties intrinsically attached to the composition in accordance with the invention are not, or not substantially, adversely affected by the intended addition or additions.

The composition according to the invention may take various forms, such as the form of liquids, creams, gels, or any other form appropriate for colouring and/or bleaching keratin fibres, and especially human keratin fibres such as the hair.

The composition according to the invention may further comprise one or more oxidation bases and/or one or more couplers and/or one or more direct dyes.

When the composition according to the invention comprises one or more oxidation bases and/or one or more couplers and/or one or more direct dyes, said composition is then a colouring composition.

When the colouring composition comprises, as dye, one or more oxidation bases optionally in combination with one or more couplers, said composition is then an oxidation colouring composition.

The oxidation base or bases are selected from oxidation bases which are conventionally used for oxidation colouring. As examples, the oxidation bases may be selected from para-phenylenediamines, bisphenylalkylenediamines, para-aminophenols, ortho-aminophenols and heterocyclic bases and their addition salts with an acid or with an alkaline agent.

The para-phenylenediamines include more particularly, by way of example, para-phenylenediamine, para-toluoylenediamine, 2-chloro-paraphenylenediamine, 2,3-dimethyl-paraphenylenediamine, 2,6-dimethyl-para-phenylenediamine, 2,6-diethyl-para-phenylenediamine, 2,5-dimethyl-para-phenylene diamine, N,N-dimethyl-para-phenylenediamine, N,N-diethyl-para-phenylenediamine, N,N-dipropyl-paraphenylenediamine, 4-amino-N,N-diethyl-3-methylaniline, N,N-bis(β-hydroxyethyl)-para-phenylenediamine, 4-N,N-bis(β-hydroxyethyl)amino 2-methylaniline, 4-N,N-bis(β-hydroxyethyl)amino 2-chloro-aniline, 2-β-hydroxyethyl-para-phenylenediamine, 2-fluoro-para-phenylenediamine, 2-isopropyl-para-phenylenediamine, N-(β-hydroxy-propyl)-para-phenylenediamine, 2-hydroxymethyl-para-phenylenediamine, N,N-dimethyl-3-methylpara-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxyparaphenylenediamine, 2-β-acetylaminoethyloxy-para-phenylenediamine, N-β-methoxyethyl)-para-phenylenediamine and 4'-aminophenyl-1-(3hydroxy)pyrrolidine, and their addition salts with an acid or with an alkaline agent.

Of the abovementioned para-phenylenediamines, particular preference is given to para-phenylenediamine, para-toluoylenediamine, 2-isopropyl-para-phenylenediamine, 2-β-hydroxyethyl-paraphenylenediamine, 2-β-hydroxyethyloxy-para-phenylenediamine, 2,6-dimethyl-para-phenylenediamine, 2,6-diethyl-para-phenylenediamine, 2,3-dimethylparaphenylenediamine, N,N-bis(β-hydroxyethyl)-paraphenylenediamine, 2-chloro-para-phenylenediamine, 2-β-acetylaminoethyloxypara-phenylenediamine, and their addition salts with an acid or with an alkaline agent.

The bisphenylalkylenediamines include more particularly, by way of example, N,N'-bis(β-hydroxyethyl)-N,N'-bis(4'-aminophenyl)-1,3-diamino-propanol, N,N'-bis(β-hydroxyethyl)-N,N'-bis(4'-aminophenyl)ethylenediamine, N,N'-bis(4-aminophenyl)tetra-methylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,5-dioxaoctane, and their addition salts with an acid or with an alkaline agent.

The para-aminophenols include more particularly, by way of example, para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and their addition salts with an acid or with an alkaline agent.

The ortho-aminophenols include more particularly, by way of example, 2-aminophenol, 2-amino-5-methylphenol, 2-amino-6-methylphenol, 5-acetamido-2-aminophenol, and their addition salts with an acid or with an alkaline agent.

The heterocyclic bases include more particularly, by way of example, pyridine derivatives, pyrimidine derivatives and pyrazole derivatives and their addition salts with an acid or with an alkaline agent. Mention may be made particularly of 1-β-hydroxyethyl-4,5-diaminopyrazole, 2,3-diamino-6,7-dihydro-1H,5H-pyrazolo[1,2-a]pyrazol-1-one and their salts.

When used, the oxidation base or bases represent preferably from 0.005% to 15% by weight, and more preferably from 0.01% to 10% by weight, relative to the total weight of the composition.

The coupler or couplers are selected from couplers conventionally used for oxidation colouring. As examples, the coupler or couplers are selected from couplers which are customarily used for the dyeing of keratin fibres. Of these couplers, mention may be made in particular of meta-phenylenediamines, meta-aminophenols, meta-diphenols, naphthalenic couplers, heterocyclic couplers and their addition salts with an acid or with an alkaline agent.

These couplers are selected more particularly from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethylpyrazolo[3,2-c]-1,2,4-triazole, 6-methylpyrazolo[1,5-a]-benzimidazole, and their addition salts with an acid or with an alkaline agent.

When present, the coupler or couplers represent preferably from 0.001% to 15% by weight, and more preferably from 0.05% to 10% by weight, relative to the total weight of the composition.

Generally speaking, the addition salts of the oxidation bases and of the couplers which can be used in the context of the invention are selected in particular from addition salts with an acid, such as hydrochlorides, hydrobromides, sulphates, citrates, succinates, tartrates, tosylates, benzenesulphonates, phosphates and acetates, and addition salts with a base such as sodium hydroxide, potassium hydroxide, ammonia, amines or alkanolamines.

When the colouring composition contains neither oxidation bases nor couplers but does contain direct dyes, said composition is an optionally lightening direct colouring composition.

The direct dye or dyes which can be used in the colouring composition may be selected from neutral, acidic or cationic nitro dyes of the benzene series, neutral, acidic or cationic direct azo dyes, neutral, acidic or cationic direct quinone— and especially anthraquinone—dyes, direct azine dyes, direct triarylmethane dyes, direct indoamine dyes and direct natural dyes, alone or in a mixture.

The direct nitrobenzene dyes which can be used according to the invention include, without limitation, the following compounds:
1,4-diamino-2-nitrobenzene,
1-amino-2-nitro-4-β-hydroxyethylaminobenzene
1-amino-2-nitro-4-bis(β-hydroxyethyl)-aminobenzene
1,4-bis(β-hydroxyethylamino)-2-nitrobenzene
1-β-hydroxyethylamino-2-nitro-4-bis(β-hydroxyethylamino)benzene
1-β-hydroxyethylamino-2-nitro-4-aminobenzene
1-β-hydroxyethylamino-2-nitro-4-(ethyl)(β-hydroxyethyl)aminobenzene
1-amino-3-methyl-4-β-hydroxyethylamino-6-nitrobenzene
1-amino-2-nitro-4-β-hydroxyethylamino-5-chlorobenzene
1,2-diamino-4-nitrobenzene
1-amino-2-β-hydroxyethylamino-5-nitrobenzene
1,2-bis(β-hydroxyethylamino)-4-nitrobenzene
1-amino-2-tris-(hydroxymethyl)-methylamino-5-nitrobenzene
1-hydroxy-2-amino-5-nitrobenzene
1-hydroxy-2-amino-4-nitrobenzene
1-hydroxy-3-nitro-4-aminobenzene
1-β-hydroxyethyloxy-2-β-hydroxyethylamino-5-nitrobenzene
1-methoxy-2-β-hydroxyethylamino-5-nitrobenzene
1-β-hydroxyethyloxy-3-methylamino-4-nitrobenzene
1-β,γ-dihydroxypropyloxy-3-methylamino-4-nitrobenzene
1-β-hydroxyethylamino-4-β,γ-dihydroxypropyloxy-2-nitrobenzene
1-β,γ-dihydroxypropylamino-4-trifluoromethyl-2-nitrobenzene
β-hydroxyethylamino-4-trifluoromethyl-2-nitrobenzene
1-β-hydroxyethylamino-3-methyl-2-nitrobenzene
1-β-aminoethylamino-5-methoxy-2-nitrobenzene
1-hydroxy-2-chloro-6-ethylamino-4-nitrobenzene
1-hydroxy-2-chloro-6-amino-4-nitrobenzene
1-hydroxy-6-bis(β-hydroxyethyl)-amino-3-nitrobenzene
1-β-hydroxyethylamino-2-nitrobenzene
1-hydroxy-4-β-hydroxyethylamino-3-nitrobenzene.

The direct azo dyes which can be used according to the invention include the cationic azo dyes described in patent applications WO 95/15144, WO 95/01772, EP 714954, FR 2 822 696, FR 2 825 702, FR 2 825 625, FR 2 822 698, FR 2 822 693, FR 2 822 694, FR 2 829 926, FR 2 807 652, WO 02/078660, WO 02/100834, WO 02/100369 and FR 2 844 269, whose content forms an integral part of the invention.

Of these compounds, mention may be made particularly of the following dyes:
1,3-dimethyl-2-[[4-(dimethylamino)phenyl]azo]-1H-imidazolium chloride,
1,3-dimethyl-2-[(4-aminophenyl)azo]-1H-imidazolium chloride,
1-methyl-4-[(methylphenylhydrazono)methyl]-pyridinium methyl sulphate.

Mention may also be made, among the direct azo dyes, of the following dyes, which are described in the third edition of the Colour Index International:
Acid Yellow 9
Acid Black 1
Basic Red 22
Basic Red 76
Basic Yellow 57
Basic Brown 16
Acid Yellow 36
Acid Orange 7
Acid Red 33
Acid Red 35

Basic Brown 17
Acid Yellow 23
Acid Orange 24.

Mention may also be made of 1-(4'-aminodiphenylazo)-2-methyl-4-bis(β-hydroxyethyl)aminobenzene and of 4-hydroxy-3-(2-methoxyphenylazo)-1-naphthalenesulphonic acid.

Of the direct quinone dyes, mention may be made of the following dyes:
Acid Violet 43
Acid Blue 62
Basic Blue 22
Basic Blue 99
and also of the following compounds:
1-N-methylmorpholiniopropylamino-4-hydroxy-anthraquinone
1-aminopropylamino-4-methylaminoanthraquinone
1-aminopropylaminoanthraquinone
5-β-hydroxyethyl-1,4-diaminoanthraquinone
2-aminoethylaminoanthraquinone
1,4-bis(β,γ-dihydroxypropylamino)anthraquinone.

Of the azine dyes, mention may be made of the following compounds:
Basic Blue 17
Basic Red 2.

Of the triarylmethane dyes which can be used according to the invention, mention may be made of the following compounds:
Basic Green 1
Acid Blue 9
Basic Violet 3
Basic Violet 14
Basic Blue 7
Acid Violet 49
Basic Blue 26
Acid Blue 7.

Of the indoamine dyes which can be used according to the invention, mention may be made of the following compound:
2-β-hydroxyethylamino-5-[bis(β-4'-hydroxyethyl)amino]anilino-1,4-benzoquinone.

Among the natural direct dyes which can be used according to the invention, mention may be made of carminic acid, kermesic acid, purpurogallin, protocatechaldehyde, isatin, curcumin, spinulosin and apigenidin, and the orceins. Use may also be made of extracts or decoctions which contain these natural dyes, and especially the henna-based poultices or extracts.

The direct dye or dyes represent preferably from 0.001% to 20% by weight, approximately, of the total weight of the colouring composition, and more preferably from 0.005 to 10% by weight, approximately.

When the composition according to the invention contains no dye but does contain one or more oxidizing agents, said composition is then a composition for bleaching keratin fibres.

Bleaching for the purposes of the present invention means the total or partial destruction of the natural pigments present in the keratin fibres (in particular, eumelanins and phaeomelanins).

The colouring and/or bleaching composition may take various forms, such as the form of liquids, creams, gels, or any other form appropriate for dyeing or for bleaching keratin fibres, and especially human keratin fibres such as the hair.

The present invention also provides a method of oxidation-colouring keratin fibres, and especially human keratin fibres such as the hair, which involves applying to said fibres a colouring composition as defined above, comprising, as dye(s), one or more oxidation bases, optionally in combination with one or more couplers and/or one or more direct dyes, in the presence of one or more oxidizing agents, for a time sufficient to develop the desired coloration.

After a leave-on time of 5 minutes to 1 hour, preferably of 10 minutes to 1 hour approximately, the keratin fibres are rinsed, washed with shampoo, rinsed again and then dried.

The oxidizing agent may be added to the colouring composition at the exact time of use, or it may be employed on the basis of an oxidizing composition containing it, which is applied simultaneously or sequentially to the colouring composition.

In one embodiment the present invention further provides a method of directly colouring, with optional lightening-keratin fibres, and especially human keratin fibres such as the hair, which involves applying to said fibres a colouring composition as defined above, comprising, as dye(s), one or more direct dyes, optionally in the presence of one or more oxidizing agents, for a time sufficient to give the desired coloration and, optionally, the desired lightening.

The present invention likewise provides a method of bleaching keratin fibres, and especially human keratin fibres such as the hair, which involves applying to said fibres a composition comprising one or more alkanolamines, one or more amino acids and one or more associative polymers in the presence of one or more oxidizing agents, leaving the composition to act for a leave-on time which is sufficient to give the required bleaching, removing the composition by rinsing with water, followed by washing with a shampoo and then, where appropriate, by drying.

The leave-on time ranges between 5 minutes and 1 hour approximately, more preferably between 10 minutes and 1 hour approximately.

Further provided by the invention is a multiple-compartment device for the dyeing or bleaching of keratin fibres, especially human keratin fibres. A first compartment contains a composition comprising one or more alkanolamines, one or more amino acids, one or more associative polymers and, where appropriate, one or more oxidation bases and/or one or more couplers and/or one or more direct dyes, and a second compartment, containing an oxidizing composition comprising one or more oxidizing agents.

The examples which follow illustrate the invention, without having any limitative character.

EXAMPLES

In the table below, a.s. signifies active substance.

|  | Amount (g %) | | | |
| --- | --- | --- | --- | --- |
|  | A | B | C | D |
| Lauric acid | 3 | 3 | 3 | 3 |
| Glycol distearate | 2 | 2 | 2 | 2 |
| Cetylstearyl alcohol (C16/C18 50/50) | 11.5 | 11.5 | 11.5 | 11.5 |
| Ethoxylated lauryl alcohol (12EO) | 7 | 7 | 7 | 7 |
| Ethoxylated oleocetyl alcohol (30EO) | 4 | 4 | 4 | 4 |
| Ethoxylated decyl alcohol (3EO) | 10 | 10 | 10 | 10 |
| Carbomer | 0.4 | 0.4 | 0.4 | 0.4 |
| Silica | 1.2 | 1.2 | 1.2 | 1.2 |
| Propylene glycol | 10 | 10 | 10 | 10 |
| Polydimethyldiallylammonium chloride, 40% in water | 2 (0.8 | 2 (0.8 | 2 (0.8 | 2 (0.8 |

-continued

| | Amount (g %) | | | |
|---|---|---|---|---|
| | A | B | C | D |
| (Polyquaternium-6) | a.s.) | a.s.) | a.s.) | a.s.) |
| DTPA (diethylenetriamine-pentaacetic acid, pentasodium salt) 40% in aqueous solution | 2 (0.8 a.s.) | 2 (0.8 a.s.) | 2 (0.8 a.s.) | 2 (0.8 a.s.) |
| Sodium metabisulphite | 0.7 | 0.7 | 0.7 | 0.7 |
| Erythorbic acid | 0.3 | 0.3 | 0.3 | 0.3 |
| Polyquaternium-24 (QUATRISOFT LM 200, sold by Amerchol) | 0.15 | 0.2 | / | / |
| Cetylhydroxyethylcellulose (Natrosol plus grade 330 CS sold by Aqualon-Hercules) | / | / | 0.3 | 0.3 |
| Monoethanolamine | 6.2 | 4.2 | 1.2 | 6.2 |
| 2-Amino-2-methylpropan-1-ol | / | / | 3 | / |
| Arginine | 3 | 3 | / | / |
| Lsyine | / | / | 4 | / |
| Hystidine | / | / | / | 3 |
| Sodium metasilicate | / | 2 | / | / |
| para-Phenylenediamine | 0.62 | / | 0.62 | 0.62 |
| para-Aminophenol | 0.09 | 0.1 | 0.09 | 0.09 |
| 2,3-Diamino-6,7-dihydro-1H,5H-pyrazolo [1,2-a] pyrazol-1-one dimethosulphonate | 1.5 | 1.9 | 1.5 | 1.5 |
| 6-Hydroxyindole | 0.2 | / | 0.2 | 0.2 |
| 1-methyl-2-hydroxy-4-amino benzene | 1.6 | 0.2 | 1.6 | 1.6 |
| 5-Amino-6-chloro-o-cresol | / | 0.8 | / | / |
| Perfume | 0.95 | 0.95 | 0.95 | 0.95 |
| Nacre (mica/titanium oxide) | 0.2 | 0.2 | 0.2 | 0.2 |
| Deionized water | qs100 | qs100 | qs100 | qs100 |

Colouring compositions A, B, C and D are mixed, at the time of use, in a plastic bowl and for 2 minutes with an aqueous oxidizing composition containing 6% hydrogen peroxide and having a pH of 2.3, in a proportion of 1 part by weight of colouring composition to 1.5 parts by weight of oxidizing composition.

The resulting mixtures do not have unpleasant odours. They are applied for 30 minutes at ambient temperature to brown hair.

After rinsing and drying, the hair is dyed uniformly.

The invention claimed is:

1. A cosmetic composition for treating keratin fibers, comprising, in a cosmetically acceptable medium:
    at least one alkanolamine;
    at least one amino acid; and
    at least one associative polymer,
wherein the alkanolamine/acid molar ratio is less than or equal to 10.

2. A cosmetic composition according to claim 1, wherein the at least one alkanolamine is chosen from monoethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol, and tris-hydroxymethylamino-methane.

3. A cosmetic composition according to claim 2, wherein the alkanolamine is monoethanolamine.

4. A cosmetic composition according to claim 1, wherein the at least one amino acid is chosen from the compounds of formula:

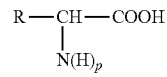

in which:
    p is 1 or 2,
    R represents a hydrogen atom, an aliphatic group containing or not containing a heterocyclic moiety, or an aromatic group; and
when p=1, R may also form, with the nitrogen atom of —N(H)$_p$, a heterocycle.

5. A cosmetic composition according to claim 4, wherein the at least one amino acid is selected from arginine, glycine, histidine, and lysine.

6. A cosmetic composition according to claim 4, wherein the at least one associative polymer is chosen from anionic, cationic, amphoteric and non-ionic associative polymers.

7. A cosmetic composition according to claim 6, wherein the at least one associative polymer is chosen from cationic and non-ionic associative polymers.

8. A cosmetic composition according to claim 1, wherein the at least one associative polymer is chosen from polyurethanes and cellulose derivatives.

9. A cosmetic composition according to claim 1, further comprising at least one entity chosen from oxidation bases, couplers, and direct dyes.

10. A cosmetic composition according to claim 1, comprising at least one oxidizing agent.

11. A method of coloring and/or lightening keratin fibers comprising:
    applying to said fibers a composition comprising, in a cosmetically acceptable medium:
        at least one alkanolamine;
        at least one amino acid;
        at least one associative polymer;
        at least one entity chosen from oxidation bases, couplers, and direct dyes; and
        optionally at least one oxidizing agent,
        wherein the alkanolamine/amino acid molar ratio is less than or equal to 10; and
    leaving the composition on the fibers for a period of time sufficient to develop the coloration and/or lightening.

12. A method of coloring and/or lightening keratin fibers according to claim 11, wherein the composition further comprises at least one oxidizing agent.

13. A method of bleaching keratin fibers, comprising
    applying to said fibers a composition comprising, in a cosmetically acceptable medium:
        at least one alkanolamine;
        at least one amino acid;
        at least one associative polymer; and
        at least one oxidizing agent,
        wherein the alkanolamine/amino acid molar ratio is less than or equal to 10; and
    leaving the composition on the fibers for a time sufficient to give the desired bleaching.

14. A multiple-compartment device for the dyeing of keratin fibers, comprising a first compartment containing a cosmetic composition comprising, in a cosmetically acceptable medium:
    at least one alkanolamine;
    at least one amino acid;
    at least one associative polymer; and at least one entity chosen from oxidation bases, couplers, and direct dyes, wherein the alkanolamine/amino acid molar ratio is greater less than or equal to 10; and a second compartment containing an oxidizing composition comprising at least one oxidizing agent.

15. A multiple-compartment device for the bleaching of keratin fibers, comprising in a first compartment containing a composition comprising, in a cosmetically acceptable medium:

at least one alkanolamine;
at least one amino acid;
at least one associative polymer; and
at least one oxidizing agent, wherein the alkanolamine/amino acid molar ratio is greater less than or equal to 10; and a second compartment containing an oxidizing composition comprising at least one oxidizing agent.

* * * * *